United States Patent [19]

Miyazawa et al.

[11] Patent Number: 5,395,983
[45] Date of Patent: Mar. 7, 1995

[54] PROCESS FOR PRODUCING 1-PHENYL-1,3-PROPANEDIOLS HAVING HIGH OPTICAL PURTIY

[75] Inventors: Kazutoshi Miyazawa; Teruyo Sugiura; Yasuyuki Koizumi; Naoyuki Yoshida, all of Ichihara, Japan

[73] Assignee: Chisso Corporation, Osaka, Japan

[21] Appl. No.: 182,566

[22] Filed: Jan. 18, 1994

Related U.S. Application Data

[63] Continuation-in-part of Ser. No. 77,129, Jun. 16, 1993, abandoned.

[30] Foreign Application Priority Data

Jul. 23, 1992 [JP] Japan ................... 4-216661

[51] Int. Cl.⁶ .............. C07C 29/78; C07C 29/76; C07C 33/26
[52] U.S. Cl. .................... 568/810; 568/715; 568/811; 568/814
[58] Field of Search .......... 568/811, 812, 648

[56] References Cited

U.S. PATENT DOCUMENTS

| | | | |
|---|---|---|---|
| 4,982,016 | 1/1991 | Choi | 568/814 |
| 5,019,658 | 5/1991 | Cahn | 568/829 |
| 5,066,815 | 11/1991 | Sayo et al. | 568/811 |

FOREIGN PATENT DOCUMENTS

| | | | |
|---|---|---|---|
| 2134334 | 5/1990 | Japan | 568/811 |
| 5-208927 | 8/1993 | Japan | 568/811 |

OTHER PUBLICATIONS

J. Org. Chem., vol. 53 No. 17 (1988) pp. 4081–4084.
Eliel, Stereochemistry of Carbon Compounds, McGraw–Hill Book Company, Inc. (1962) pp. 47–49.

*Primary Examiner*—Werren B. Lone
*Attorney, Agent, or Firm*—Wenderoth, Lind & Ponack

[57] ABSTRACT

R or S-1-phenyl-1,3-propanediols having optical purity of 100% ee were obtained by recrystallization of R or S-1-phenyl-1,3-propanediols having optical purity of 20% ee to below 100% ee, the last diols are represented by the formula,

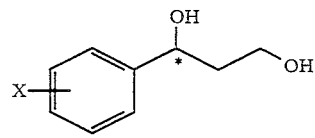

It is possible to obtain optically pure 1-phenyl-3-propanediols from optically impure 1-phenyl-1,3-propanediols by a simple method.

7 Claims, 5 Drawing Sheets

PROCESS FOR PRODUCING 1-PHENYL-1,3-PROPANEDIOLS HAVING HIGH OPTICAL PURTIY

This application is a continuation-in-part of now abandoned application Ser. No. 08/077,129, filed Jun. 16, 1993.

BACKGROUND OF THE INVENTION

1. Field of the Invention

The present invention relates to a process for producing optically active and physiologically active compounds, particularly optically active compounds having high optical purity useful as starting materials for tomoxetine, fluoxetine and the like, namely optically active 1-phenyl-1,3-propanediols.

2. Description of the Prior Art

Tomoxetine and fluoxetine that are useful as antidepressants have two kinds of optical isomers because they have an asymmetric carbon atom. In the isomers, S-compounds alone have effect as antidepressants. For practical purposes, it is necessary to use the S-compounds alone, because the racemates or compounds having low optical purity do not show sufficient physiological activity (Drugs Future, 11, 134(1986), S. I. Ankier, Prog. Med. Chem., 23, 121(1986)).

When optically active tomoxetine or fluoxetine is produced, optically active 1-phenyl-1,3-propanediol is usefull, as a starting material. However, there is little literature of methods for obtaining optically active 1-phenyl-1,3-propanediol having high optical purity, so that it is long-awaited to find a simple purification method for easily improving the optical purity (Y. Gao and K. B. Sharpless, J. Org. Chem., 53, 4081(1988)).

Furthermore, though physiological activity of analogues of tomoxetine or fluoxetine having a substituted group on the phenyl group has not been studied, revelation of higher physiological activity is expected by the effect of the substituted group.

The present invention provides a simple purification method for easily improving optical purity to efficiently obtain optically active 1-phenyl-1,3-propanediols having high optical purity.

SUMMARY OF THE INVENTION

Namely, the present invention resides in a process for producing an optically active 1-phenyl-1,3-propanediol having high otical purity characterized in that it comprises recrystalizing an R or S-1-phenyl-1,3-propanediol having purity of 20% ee to below 100% ee from a solvent, the diol being represented by the formula,

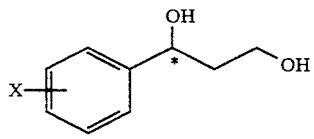

wherein X is a halogen atom or alkoxy of 1–4 carbon atoms, and obtaining an R or S-1-phenyl-1,3-propanediol having optical purity of 100% ee.

The above R or S-1-phenyl-1,3-propanediol having purity of 20% ee to below 100% ee is obtained, for example, by methods described by Uehara et al. (Japanese Unexamined Patent Publication No. 4-258297) and Matsuyama et al. (Japanese Unexamined Patent Publication No. 4-58896). Namely, Uehara et al. teaches a process for producing an optically active 1-phenyl-1,3-propanediol and its derivative having an optically purity of 21.4% ee to 93.2% ee prepared by a process comprising effecting a hydrolase to an enantiomeric mixture of compounds represented by the general formula,

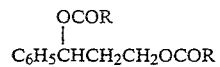

wherein R represents a linear or branched alkyl group or alkenyl group of 1 to 9 carbon atoms. Further, Matsuyama et al. teaches a process for producing an optically active 1-phenyl-1,3-propanediol having an optically purity of 55% ee to 95% ee prepared by a process comprising effecting microorganisms to an enantiomeric mixture of 1-phenyl-1,3-propanediol and obtaining a resultant optically active 1-phenyl-1,3-propanediol.

The present invention is attained by dissolving optically impure 1-phenyl-1,3-propanediols in solvents under an elevated temperature, cooling the solution to precipitate crystals at atmospheric pressure and in the absence of seeding, removing the crystalized 1-phenyl-1,3-propanediols from the solvents, and obtaining optically pure 1-phenyl-1,3-propanediols.

In the present invention, though it is able to use the optically impure 1-phenyl-1,3-propanediols having purity of 20% ee to below 100% ee as starting raw material, such diols having higher optical purity in the above range give purified product diols in good yield.

Solvents which can dissolve optically impure 1-phenyl-1,3-propanediols are used in the present invention. Preferably, aliphatic hydrocarbons such as pentane, hexane, heptane and octane, alicyclic hydrocarbons such as cyclopentane and cyclohexane, esters such as methyl acetate, ethyl acetate, methyl propionate and ethyl propionate, ethers such as diethyl ether and diisopropyl ether, aromatic compounds such as benzene, toluene and xylene, alcohols such as methanol, ethanol and propanol, glycols such as ethylene glycol and diethylene glycol, and water and mixtures of any of these solvents are used.

Further, the crystallization of optically pure 1-phenyl-1,3-propanediols in solvents in the present invention can be conducted by heating to dissolve the diols into the solvents and cooling as it is, or by dissolving the diols into the hot solvents and cooling the solution.

The present invention can provide optically pure 1-phenyl-1,3-propanediols by purifying optically impure 1-phenyl-1,3-propanediols by .using a very simple technique of recrystallization.

DESCRIPTION OF THE PREFERRED EMBODIMENTS

The following illustrates the present invention by typical examples. The optical purity of optically active 1-phenyl-1,3-propanediols in the examples was determined by either of following two methods.

Method 1

When R- and S-diols could be separated with an optical resolution column, the optical purity was determined by liquid chromatography using the optical resolution column. As the optical resolution column, CHIRAL CEL OB (manufactured by Daicel Co., Ltd., trade name) was preferably used.

Method 2

When R- and S-diols could not be separated with an optical resolution column, the optical purity was determined by using capillary gas chromatographic analysis of diastereomers that had been systhesized from 1-phenyl-1,3-propanediols and (−)-menthone according to the following scheme.

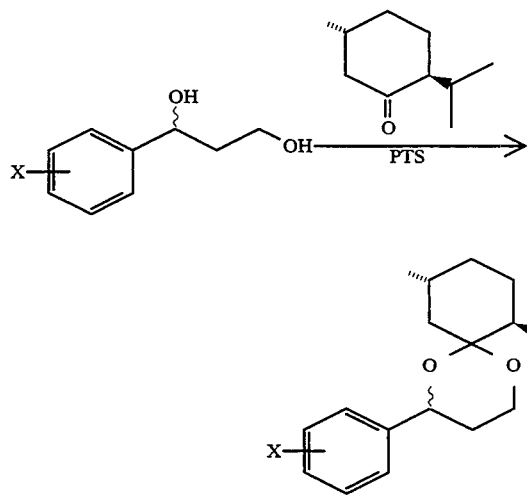

-continued

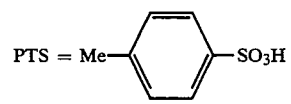

PTS = Me—⟨⟩—SO$_3$H

Figure 5:
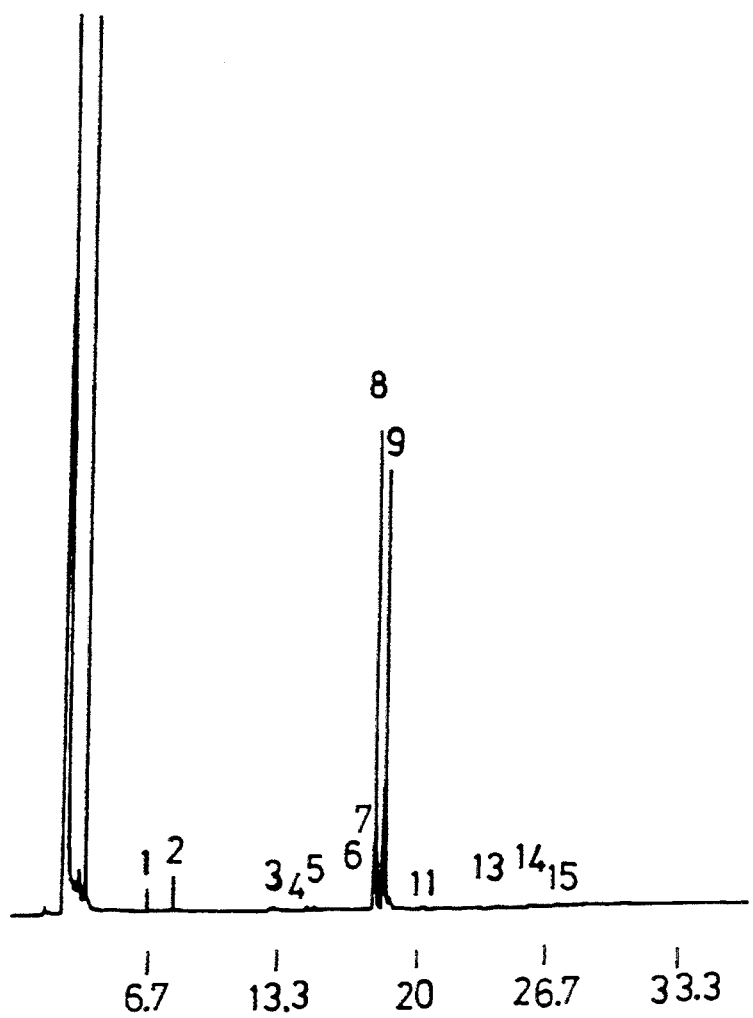
FIG. 5 shows a capillary gas chromatography of the diastereomer compound that was sysnthesized from racemic 1-(4-methoxyphenyl)-1,3-propanediol and (−)-menthone. When the 1-phenyl-1,3-propanediols which were used in the diastereomer synthesis are optically active compounds, the optical purity can be determined by the area ratio of peak No. 8 (retention time of 18.05 minutes) and peak No. (retention time of 18.77 minutes).

FIG. 5 shows the chromatogram of capillary gas chromatographic analysis of diastereomers (in the above scheme, X is methoxy) synthesized from racemic 1-(4-methoxyphenyl)-1,3-propanediol and (−)-menthone. The peaks derived from each diastereomer are completely separated and the optical purity is determined from these peaks.

Example 1

To 100 ml of toluene, 100 g of R-1-phenyl-1,3-propanediol having optical purity of 57.7% ee was dissolved by heating, and the solution was cooled to room temperature at atmospheric pressure and in the absence of seeding, to crystallize one of R and S-1-phenyl-1,3-propanediol corresponding to an enantiomeric excess side. Precipitated crystals were collected by suction filtration to collect the crystals and dried under reduced pressure to obtain 54 g of R-1-phenyl-1,3-propanediol as colorless needles. Yield 54%.

$[\alpha]_D^{28}$ +69.5° (c1.09, CHCl$_3$)

Melting point: 61.8°–63.4° C.

$^1$H-NMR (90 MHz, CDCl$_3$, internal standard TMS); δ:7.34(s, 5H), 4.94(q, 1H), 3.84(t, 2H), 2.65(brs, 2H), 2.07–1.92(m, 2H).

Further, the optical purity determined by liquid chromatography using an optical resolution column above-mentioned in Method 1 was 100% ee. (Determination Conditions, column: CHIRAL CEL OB (25 cm×0.46 cm, Daicel Co., Ltd.), solvent: hexane/isopropanol (9/1), flow rate: 0.5 ml/min)

Figure 1:
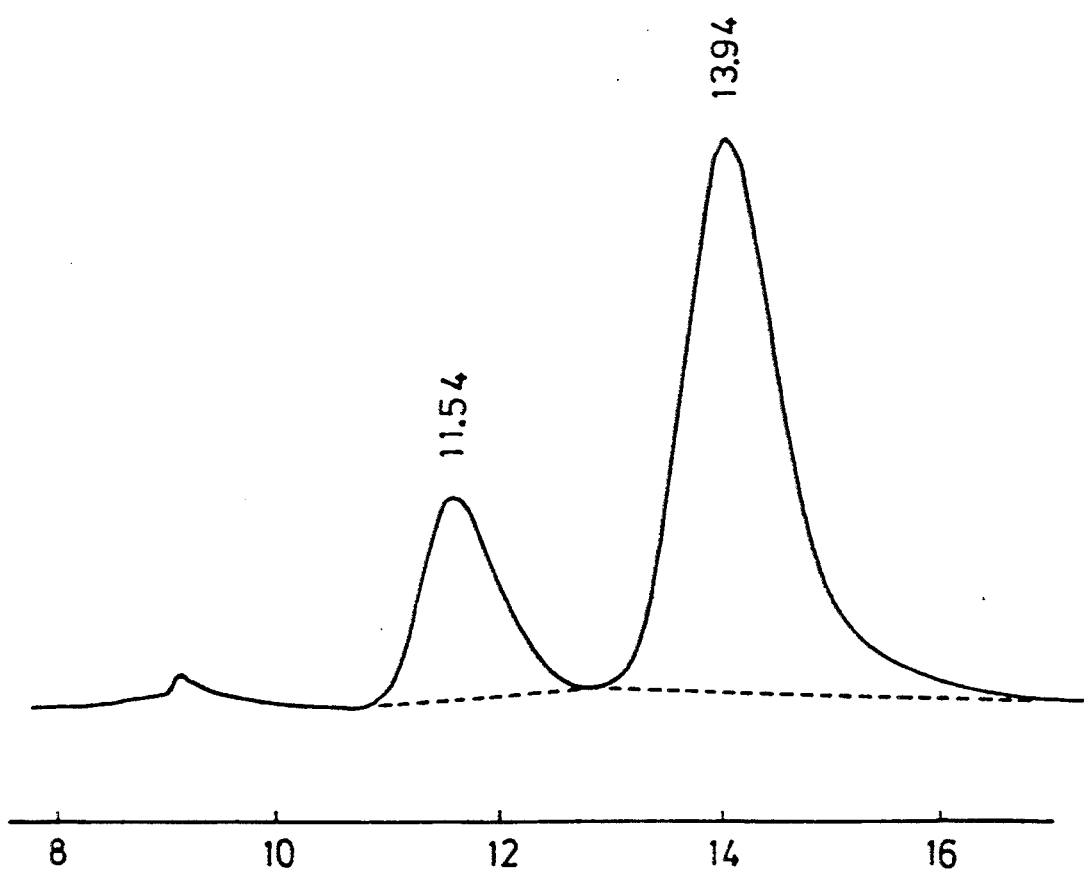
FIG. 1 shows a liquid chromatography analysis chart of R-1-phenyl-1,3-propanediol having optical purity of 57.7% ee that was used in Example 1. The peak at a retention time of 11.5 minutes (a number above the peak) shows S-1-phenyl-1,3-propanediol and the peak at a retention time of 13.94 minutes shows R-1-phenyl-1,3-propanediol. The areas of these peaks show contents of each compound.
Figure 2:
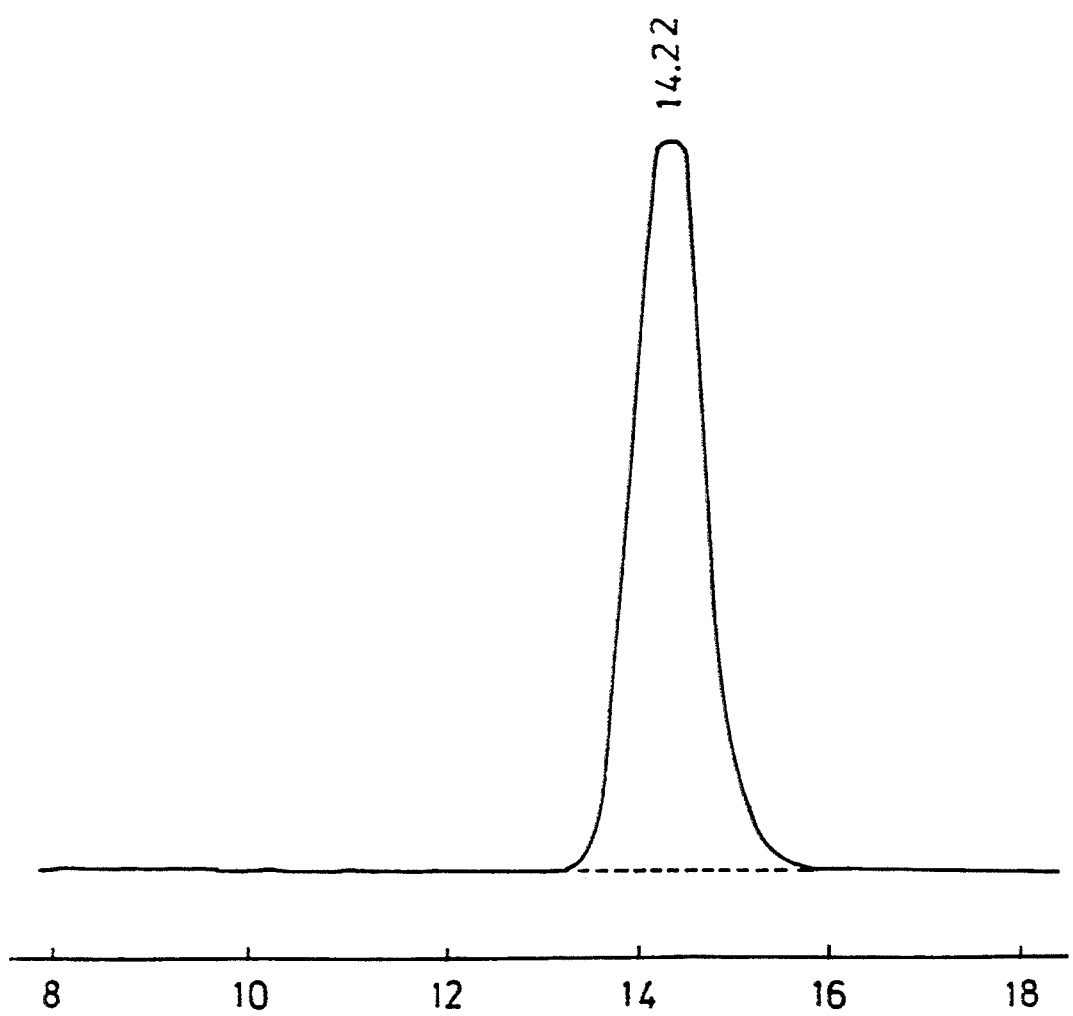
FIG. 2 shows a liquid chromatography analysis chart of R-1-phenyl-1,3-propanediol having optical purity of 100% ee that was prepared in Example 1. The peak at a retention time of 14.22 minutes shows R-1-phenyl-1,3-propanediol.

FIG. 1 shows a liquid chromatography analysis chart of R-1-phenyl-1,3-propanediol having optical purity of 57.7% ee that was used as a starting material, and FIG. 2 shows a liquid chromatography analysis chart of R-1-phenyl-1,3-propanediol having optical purity of 100% ee that was prepared.

Example 2

After 100 g of S-1-phenyl-1, 3-propanediol having optical purity of 74.8% ee was dissolved by heating in 600 ml of mixed solvent of heptane/ethyl acetate (9/5), the solution was allowed to cool to room temperature at atmospheric pressure and in the absence of seeding, to crystallize one of R and S-1-phenyl-1,3-propanediol corresponding to an enantiomeric excess side. Precipitated crystals were collected by suction filtration to collect the crystals and dried under reduced pressure to obtain 71 g of S-1-phenyl-1,3-propanediol as colorless needles. Yield 71%.

$[\alpha]_D^{28}$ −68.3° (c1.34, CHCl$_3$ )

Melting point: 62.0°–63.4 ° C.

$^1$H-NMR (90 MHz, CDCl$_3$, internal standard TMS); δ:7.34(s, 5H), 4.94(q, 1H), 3.84(t, 2H), 2.65(brs, 2H), 2.07–1.92(m, 2H).

Further, the optical purity determined by liquid chromatography using an optical resolution column above mentioned in Method 1 was 100% ee. (Determination Conditions, column: CHIRAL CEL OB (25 cm×0.46 cm, Daicel Co., Ltd.), solvent: hexane/isopropanol (9/1), flow rate: 0.5 ml/min)

Figure 3:
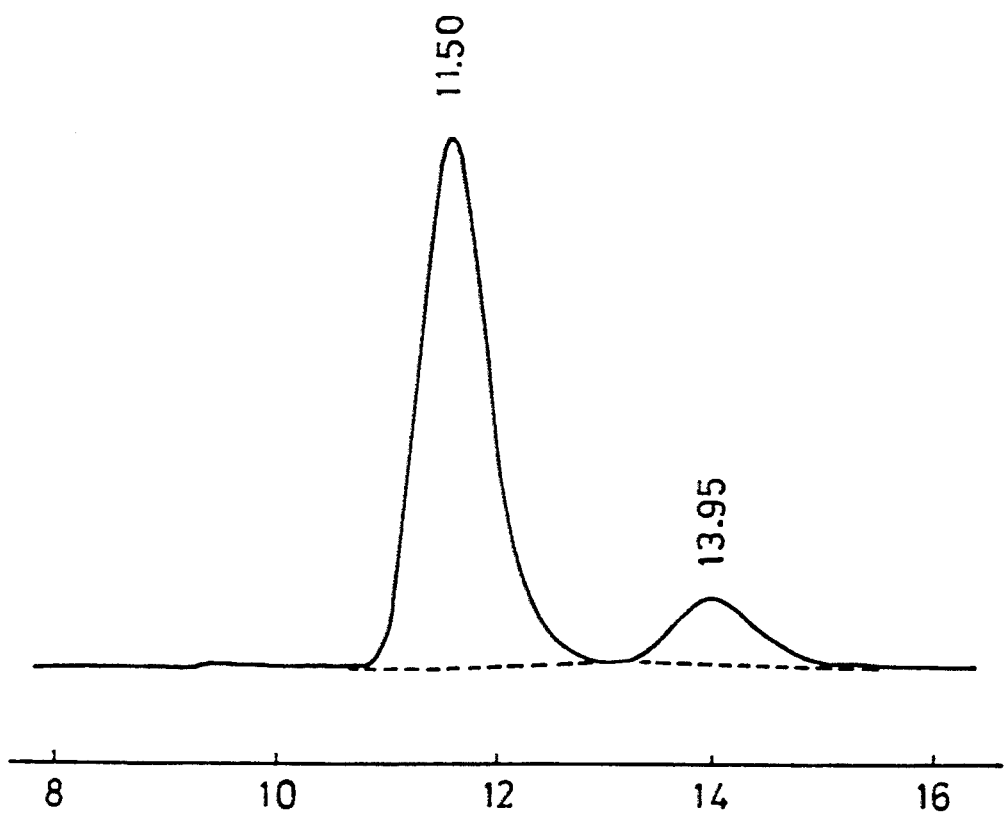
FIG. 3 shows a liquid chromatography analysis chart of S-1-phenyl-1,3-propanediol having optical purity of 74.8% ee that was used in Example 2. The peak at a retention time of 11.50 minutes shows S-1-phenyl-1,3-propanediol and the peak at a retention time of 13.95 minutes shows R-1-phenyl-1,3-propanediol. The areas of these peaks show contents of each compound.
Figure 4:
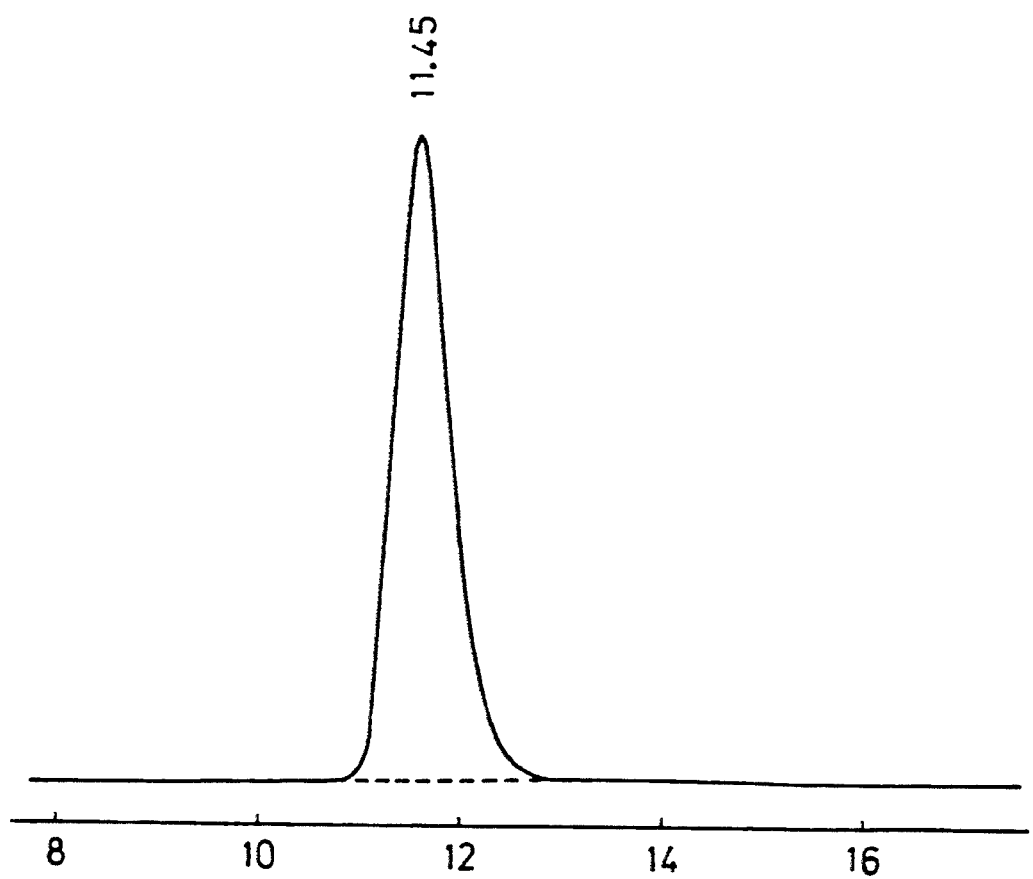
FIG. 4 shows a liquid chromatography analysis chart of S-1-phenyl-1,3-propanediol having optical purity of 100% ee that was prepared in Example 2. The peak at a retention time of 11.45 minutes shows S-1-phenyl-1,3-propanediol.

FIG. 3 shows a liquid chromatography analysis chart of S-1-phenyl-1,3-propanediol having optical purity of 74.8% ee that was used as a starting material, and FIG. 4 shows a liquid chromatography analysis chart of S-1-phenyl-1,3-propanediol having optical purity of 100% ee that was prepared.

Example 3

After 27 g of R-1-(4-fluorophenyl)-1,3-propanediol having optical purity of 78.5% ee was dissolved by heating in 40 ml of toluene, the solution was allowed to cool to room temperature at atmospheric pressure and in the absence of seeding, to crystallize one of R and S-1-phenyl- 1,3-propanediol corresponding to an enantiomeric excess side. Precipitated crystals were collected by suction filtration to collect the crystals and dried under reduced pressure to obtain 12 g of R-1-(4-fluorophenyl)-1,3-propanediol as colorless needles. Yield 44%.

$[\alpha]_D^{25} +59.4°$ (c1.06, CHCl$_1$)
Melting point: 47.7°–50.5° C.
$^1$H-NMR (90 Mhz, CDCl$_3$, internal standard TMS); δ:7.42–6.93(m, 4H), 4.95(m, 1H), 3.86(q, 2H), 2.93(d, 1H), 2.29(t, 1H), 2.06–1.85(m, 2H).

Further, the optical purity determined by above-mentioned Method 2 was 100% ee. (Determination Conditions, column: G-205(1.2 μm×40 m, Kagaku-hin Kensa Kyokai), carrier gas: helium (20 ml/min), injection temperature: 300° C., column temperature: 200° C. (1 min.-)-280° C. (5° C./min).

Example 4

After 33 g of S-1-(4-fluorophenyl)-1,3-propanediol having optical purity of 65.5% ee was dissolved by heating in 55 ml of toluene, the solution was allowed to cool to room temperature at atmospheric pressure and in the absence of seeding, to crystallize one of R and S-1-phenyl-1,3-propanediol corresponding to an enantiomeric excess side. The precipitated crystals were collected by suction filtration to collect the crystals and dried under reduced pressure to obtain 10 g of S-1-(4-fluorophenyl-1,3-propane diol) as colorless needles. Yield 30%.

$[\alpha]_D^{26} -59.4°$ (c1.01, CHCl$_3$)
Melting point: 47.7°–50.5° C. 1 H-NMR ( 90 MHz, CDCl$_3$, internal standard TMS); δ:7.42–6.93(m, 4H), 4.95(m, 1H), 3.86(q, 2H), 2.93(d, 1H), 2.29(t, 1H), 2.06–1.85(m, 2H).

Further, the optical purity determined by above-mentioned Method 2 was 100% ee. (Determination Conditions, column: G-205 (1.2 μm×40 m, Kagaku-hin Kensa Kyokai), carrier gas: helium (20 ml/min), injection temperature: 30° C., column temperature: 200° C. (1 min.-)-280° C. (5° C./min).

Example 5

After 14 g of S-1-(4-methoxyphenyl)-1,3-propanediol having optical purity of 60.0% ee ($[\alpha]_D^{26} -30.5°$ (c1.09, CHCl$_3$)) was dissolved by heating in 80 ml of mixed solvent of heptane/ethyl acetate (9/4), the solution was allowed to cool to room temperature at atmospheric pressure and in the absence of seeding, to crystallize one of R and S-1-phenyl-1,3-propanediol corresponding to an enantiomeric excess side. Precipitated crystals were collected by suction filtration to collect the crystals and dried under reduced pressure to obtain 5.3 g of S-1-(4-methoxyphenyl-1,3-propanediol ) as colorless needles. Yield 38%.

$[\alpha]_D^{31} -59.7°$ (c0.432, CHCl$_3$, internal standard TMS),
Melting point: 66.2°–67.2° C.

$^1$H-NMR (90 MHz, CDCl$_3$, internal standard TMS); δ:7.10(q, 4H), 4.86(q, 1H), 3.79(t, 2H), 3.78(s, 3H), 2.98(brs, 2H), 2.03–1.83(m, 2H).

Further, the optical purity determined by above-mentioned Method 2 was 100% ee. (Determination Conditions, column: G-205 (1.2 μm×40 m, Kagaku-hin Kensa Kyokai), carrier gas: helium (20 ml/min), injection temperature: 300° C., column temperature: 200° C. (1 min.-)-280° C. (5° C./min).

We claim:

1. A process for producing an optically active 1-phenyl-1,3-propanediol having an optical purity as 100% ee comprising the steps of (1) dissolving a R or S-1-phenyl-1,3-propanediol having an optical purity of 21.4% ee to 95% ee and represented by the formula,

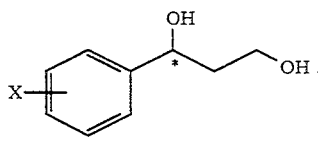

wherein X is a halogen atom or an alkoxy group of 1 to 4 carbon atoms in a solvent selected from the group consisting of an aliphatic hydrocarbon, an alicyclic hydrocarbon, an ester, an ether, an aromatic compound, an alcohol, a glycol, water and mixtures thereof at an elevated temperature above room temperature and sufficient to dissolve said diol, (2) cooling the thus obtained solution at atmospheric pressure and in the absence of seeding, to crystallize one of R and S-1-phenyl-1,3-propanediol corresponding to an enantiomeric excess side, (3) subjecting the cooled solution to a suction filtration to collect the crystals and (4) drying the collected crystals under a reduced pressure.

2. A process as claimed in claim 1, wherein R or S-1-phenyl-1,3-propanediol used as a starting raw material is a one having an optical purity of 21.4% ee to 93.2% ee and prepared by a process comprising effecting a hydrolase treatment of an enantiomeric mixture of compounds represented by the formula,

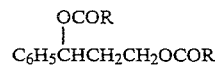

wherein R represents a linear or branched alkyl group or alkenyl group of 1 to 9 carbon atoms.

3. A process as claimed in claim 1, wherein R or S-1-phenyl-1,3-propanediol used as a starting raw material is a one having an optical purity of 55% ee to 95% ee and prepared by a process comprising treatment of an enantiomeric mixture of 1-phenyl-1,3-propanediol and obtaining a resultant optically active 1-phenyl-1,3-propanediol.

4. A process as claimed in claim 2, wherein R or S-1-phenyl-1,3-propanediol used as a starting raw material is a one having an optical purity of 57.7% ee to 78.5% ee.

5. A process as claimed in claim 1, wherein the R or S-1-phenyl-1,3-propanediol having purity of 20% ee to below 100% ee is R or S-1-phenyl-1,3-propanediol, R or S-1-(4-fluorophenyl)-1,3-propanediol, or R or S-1-(4-methoxyphenyl)-1,3-propanediol.

6. A process as claimed in claim 1, wherein the solvent is hexane, heptane, octane, cyclohexane, ethyl acetate, diethyl ether, benzene, toluene, methanol, ethanol, ethylene glycol or water or a mixture of any of these solvents.

7. A process as claimed in claim 6, wherein the solvent is heptane or toluene or a mixture of these solvents.

* * * * *